(12) United States Patent
Suzuki et al.

(10) Patent No.: US 8,722,908 B2
(45) Date of Patent: May 13, 2014

(54) METHOD FOR PRODUCING GLYCOLIDE

(75) Inventors: Shigeru Suzuki, Tokyo (JP); Kazuyuki Yamane, Tokyo (JP); Masaru Kagoshima, Tokyo (JP); Michio Kikuchi, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 13/522,435

(22) PCT Filed: Dec. 16, 2010

(86) PCT No.: PCT/JP2010/072671
§ 371 (c)(1),
(2), (4) Date: Jul. 16, 2012

(87) PCT Pub. No.: WO2011/089802
PCT Pub. Date: Jul. 28, 2011

(65) Prior Publication Data
US 2012/0289713 A1    Nov. 15, 2012

(30) Foreign Application Priority Data
Jan. 19, 2010   (JP) ................................. 2010-009017

(51) Int. Cl.
*C07D 319/00* (2006.01)
(52) U.S. Cl.
USPC ........................................................ 549/274
(58) Field of Classification Search
USPC ........................................................ 549/274
See application file for complete search history.

(56) References Cited

U.S. PATENT DOCUMENTS

| 5,830,991 A | 11/1998 | Shiiki et al. |
| 6,916,939 B2 * | 7/2005 | Yamane et al. ............... 549/274 |
| 2003/0191326 A1 | 10/2003 | Yamane et al. |
| 2004/0122240 A1 | 6/2004 | Yamane et al. |

FOREIGN PATENT DOCUMENTS

| CN | 101054371 A | 10/2007 |
| JP | A-09-328481 | 12/1997 |
| JP | A-2002-128777 | 5/2002 |
| JP | A-2004-523596 A | 8/2004 |
| WO | WO 02/14303 A1 | 2/2002 |
| WO | WO 2010/073512 A1 | 7/2010 |

OTHER PUBLICATIONS

Aug. 7, 2012 International Preliminary Report on Patentability issued in International Application No. PCT/JP2010/072671 (with translation).
Mar. 29, 2011 International Search Report issued in International Patent Application No. PCT/JP2010/072671.

* cited by examiner

*Primary Examiner* — Taylor Victor Oh
(74) *Attorney, Agent, or Firm* — Oliff PLC

(57) ABSTRACT

A method for producing glycolide, including the steps of: heating a mixture containing a glycolic acid oligomer, a high-boiling point polar organic solvent having a boiling point of 230 to 450° C., and a tin compound under normal pressure or reduced pressure until a temperature at which the glycolic acid oligomer is depolymerized, to thereby dissolve the glycolic acid oligomer in the high-boiling point polar organic solvent; heating a solution, in which the glycolic acid oligomer is dissolved, under normal pressure or reduced pressure until a temperature at which the glycolic acid oligomer is depolymerized, to thereby form glycolide by depolymerization of the glycolic acid oligomer in the solution; and co-distilling off the high-boiling point polar organic solvent and the formed glycolide from a depolymerization reaction system.

10 Claims, No Drawings

METHOD FOR PRODUCING GLYCOLIDE

TECHNICAL FIELD

The present invention relates to a method for producing glycolide, and more specifically to a method for producing glycolide obtained by depolymerizing a glycolic acid oligomer in a solvent.

BACKGROUND ART

Polyglycolic acid is a resin material having excellent biodegradability, gas-barrier property, strength, and the like, and has been used, in a wide range of technical fields, as medical polymer materials such as surgical sutures and artificial skins; packaging materials such as bottles and films; and a resin material for various industrial products such as injection molded articles, fibers, vapor-deposited films, and fishing lines.

Polyglycolic acid can be obtained by dehydration polycondensation of glycolic acid. However, the polyglycolic acid obtained by this method has a low degree of polymerization and a weight average molecular weight of 20 thousand or less. Although this polyglycolic acid has an excellent biodegradability, characteristics such as gas-barrier property, strength, and durability of the polyglycolic acid are not sufficiently satisfactory for many fields.

For this reason, polyglycolic acid is generally produced by ring-opening polymerization of glycolide. This method makes it possible to easily control the degree of polymerization of polyglycolic acid, and to obtain polyglycolic acid having a high degree of polymerization and a weight average molecular weight exceeding 20 thousand. The glycolide obtained here is generally synthesized as follows. Specifically, glycolic acid is subjected to dehydration polycondensation according to the following formula (I) to thereby synthesize a glycolic acid oligomer having a low degree of polymerization:

[Chem. 1]

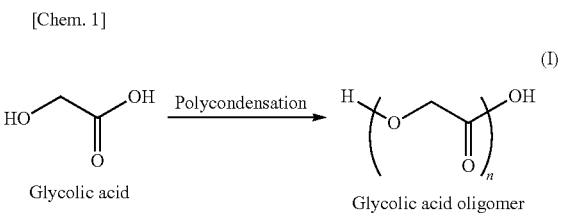

(I)

Next, the above-mentioned glycolic acid oligomer is depolymerized according to the following formula (II):

[Chem. 2]

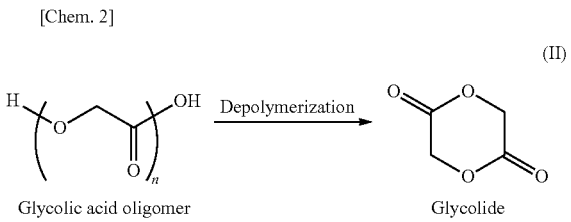

(II)

As methods for producing glycolide by such depolymerization of a glycolic acid oligomer, for example, methods for producing glycolide are proposed in which a mixture containing a glycolic acid oligomer and a high-boiling point polar organic solvent is heated to thereby dissolve the glycolic acid oligomer; the heating is continued in this state to thereby depolymerize the glycolic acid oligomer; the formed glycolide is distilled off together with the high-boiling point polar organic solvent; and then the glycolide is recovered from the distillate [for example, Japanese Unexamined Patent Application Publication No. Hei 9-328481 (PTL 1), International Publication No. WO02/014303 (PTL 2), and International Application Japanese-Phase Publication No. 2004-523596 (PTL 3)]. In particular, PTL 2 discloses that the use of a specific polyalkylene glycol ether as the high-boiling point polar organic solvent makes it possible to suppress thermal degradation of the high-boiling point polar organic solvent. In addition, PTL 2 discloses that the depolymerization reaction does not require any catalyst for the depolymerization. Moreover, PTL 3 discloses that glycolide can be efficiently produced stably for a long period by continuously or intermittently introducing the glycolic acid oligomer into a depolymerization reaction system and further by conducting the depolymerization reaction in the presence of a compound having an alcoholic hydroxyl group.

However, impurities such as glycolic acid and an open-chain dimer thereof are formed in such a depolymerization reaction of a glycolic acid oligomer, in addition to glycolide, which is the target component. Accordingly, these impurities have to be removed in order to obtain a high-purity glycolide. In addition, the impurities not only may lower the purity of glycolide, but also may cause blocking of a production line in a case where the production is continued for a long period. For this reason, it is necessary to suppress by-production of glycolic acid, an open-chain dimer thereof, and the like in the depolymerization reaction of the glycolic acid oligomer, and to thereby increase the purity of the glycolide after the depolymerization reaction.

CITATION LIST

Patent Literature

[PTL 1] Japanese Unexamined Patent Application Publication No. Hei 9-328481
[PTL 2] International Publication No. WO02/014303
[PTL 3] International Application Japanese-Phase Publication No. 2004-523596

SUMMARY OF INVENTION

Technical Problem

The present invention has been made in view of the problem of the conventional technologies, and an object of the present invention is to provide a method for producing glycolide in which a high-purity glycolide can be obtained in a case where glycolide is produced by depolymerization of a glycolic acid oligomer in a solution phase.

Solution to Problem

The present inventors have conducted earnest study to achieve the above object. As a result, the present inventors have found the following facts. Specifically, when glycolide is produced by depolymerization of a glycolic acid oligomer in a solution phase, the depolymerization in the presence of a tin compound leads to suppression of the production of glycolic acid, an open-chain dimer thereof, and the like in the depolymerization reaction, so that the purity of the obtained glycolide is improved, and moreover the yield of the glycolide is greatly increased. This findings have led to the completion of the present invention.

Specifically, a method for producing glycolide of the present invention comprises the steps of:

heating a mixture containing a glycolic acid oligomer, a high-boiling point polar organic solvent having a boiling point of 230 to 450° C., and a tin compound under normal pressure or reduced pressure until a temperature at which the glycolic acid oligomer is depolymerized, to thereby dissolve the glycolic acid oligomer in the high-boiling point polar organic solvent;

heating a solution, in which the glycolic acid oligomer is dissolved, under normal pressure or reduced pressure until a temperature at which the glycolic acid oligomer is depolymerized, to thereby form glycolide by depolymerization of the glycolic acid oligomer in the solution; and co-distilling off the high-boiling point polar organic solvent and the formed glycolide from a depolymerization reaction system.

The tin compound used in the present invention is preferably tin dichloride or tin octanoate. The high-boiling point polar organic solvent is preferably a polyalkylene glycol diether which is represented by the following formula (1) and which has a molecular weight of 150 to 450:

$$X^1-O-(R^1-O)_p-Y^1 \qquad (1)$$

(in the formula (1), $R^1$ represents a methylene group or a linear or branched alkylene group having 2 to 8 carbon atoms, $X^1$ represents a hydrocarbon group, $Y^1$ represents an alkyl group having 2 to 20 carbon atoms or an aryl group having 6 to 20 carbon atoms, p is an integer of 1 or larger, and when p is 2 or larger, a plurality of $R^1$s may be the same or different from each other).

The mixture according to the present invention preferably further contains at least one solubilizing agent having a boiling point of 180° C. or higher which is selected from the group consisting of alcohols, phenols, aliphatic carboxylic acids, aliphatic amides, aliphatic imides, polyalkylene glycol diethers having a molecular weight exceeding 450, and sulfonic acids. The solubilizing agent is preferably a polyalkylene glycol monoether represented by the following formula (2):

$$HO-(R^2-O)_q-X^2 \qquad (2)$$

(in the formula (2), $R^2$ represents a methylene group or a linear or branched alkylene group having 2 to 8 carbon atoms, $X^2$ represents a hydrocarbon group, q is an integer of 1 or larger, and when q is 2 or larger, a plurality of $R^2$s may be the same or different from each other).

Advantageous Effects of Invention

According to the present invention, it is possible to improve the purity of glycolide, and greatly increase the yield of glycolide in a case where glycolide is produced by depolymerization of a glycolic acid oligomer in a solution phase.

DESCRIPTION OF EMBODIMENTS

Hereinafter, the present invention will be described in detail based on preferred embodiments thereof.

A method for producing glycolide of the present invention includes the steps of:

heating a mixture containing a glycolic acid oligomer, a high-boiling point polar organic solvent, and a tin compound under predetermined conditions, to thereby dissolve the glycolic acid oligomer in the high-boiling point polar organic solvent;

heating the thus obtained solution under predetermined conditions, to thereby form glycolide by depolymerization of the glycolic acid oligomer in the solution; and co-distilling off the high-boiling point polar organic solvent and the formed glycolide from a depolymerization reaction system.

(1) Glycolic Acid Oligomer

The glycolic acid oligomer used in the present invention is a polyglycolic acid having a weight average molecular weight of 20 thousand or less. The glycolic acid oligomer can be synthesized by a polycondensation reaction of glycolic acid. Note that the weight average molecular weight of the glycolic acid oligomer is a value measured by gel permeation chromatography (GPC) with hexafluoroisopropanol as an eluent, and converted to that of standard polymethyl methacrylate.

An example of a method for synthesizing the glycolic acid oligomer is described below. However, the glycolic acid oligomer used in the present invention is not limited to glycolic acid oligomers synthesized by this method. For example, the glycolic acid oligomer is obtained as follows. Specifically, a polycondensation reaction or an ester-exchange reaction is conducted by heating at least one of glycolic acid, esters thereof (for example, lower alkyl esters) and salts thereof (for example, sodium salt), when necessary, in the presence of a polycondensation catalyst or an ester-exchange catalyst at a temperature of generally 100 to 250° C., and preferably 140 to 230° C., until substantially no further low-molecular weight substances such as water and alcohol are distilled off. Whereas the thus obtained glycolic acid oligomer may be used directly as a raw material in the production method of the present invention, the thus obtained glycolic acid oligomer is preferably used as the raw material after unreacted materials, components having low degrees of polymerization, the catalyst, and the like are removed by washing the obtained glycolic acid oligomer with a poor solvent such as benzene or toluene, from the viewpoint of the purity of the target glycolide.

The degree of polymerization of the glycolic acid oligomer used in the present invention is not particularly limited. The glycolic acid oligomer preferably has such a degree of polymerization that the melting point (Tm) of the glycolic acid oligomer is 140° C. or higher (more preferably 160° C. or higher, and particularly preferably 180° C. or higher). If the melting point of the glycolic acid oligomer is lower than the lower limit, the yield of the glycolide obtained by the depolymerization reaction tends to be low. Note that the melting point of the glycolic acid oligomer is a temperature detected as an endothermic peak temperature which is observed when a calorimetric analysis is conducted by using a differential scanning calorimeter (DSC) under an inert gas atmosphere and under a condition of a rate of temperature rise of 10° C./minute. An upper limit value of the melting point of the glycolic acid oligomer is approximately 220° C.

(2) High-Boiling Point Polar Organic Solvent

A high-boiling point polar organic solvent having a boiling point of 230 to 450° C. is used as a solvent in the depolymerization reaction of the glycolic acid oligomer according to the present invention. The high-boiling point polar organic solvent acts as a solvent in the depolymerization reaction, and acts as a co-distillation component when the formed glycolide is taken out from a reaction system. The latter action makes it possible to prevent adherence of glycolide and the like to an inner wall of a production line. Accordingly, if the boiling point of the high-boiling point polar organic solvent is lower than the lower limit, the depolymerization reaction temperature cannot be set to a high value, so that the formation speed of glycolide is lowered. Meanwhile, if the boiling point of the high-boiling point polar organic solvent exceeds the upper limit, the high-boiling point polar organic solvent is difficult to distill off during the depolymerization reaction, and is difficult to co-distill off with the formed glycolide. From such a viewpoint, the boiling point of the high-boiling point polar organic solvent is preferably 235 to 450° C., more preferably 255 to 430° C., and particularly preferably 280 to 420° C. Note that the boiling point of the high-boiling point polar organic solvent in the present invention is a value under normal pressure, and when a boiling point is measured under a reduced pressure, the boiling point is converted to the value under normal pressure.

The molecular weight of the high-boiling point polar organic solvent is preferably 150 to 450, more preferably 180 to 420, and particularly preferably 200 to 400. If the molecular weight of the high-boiling point polar organic solvent is out of the range, the co-distilling off with glycolide tends to be less likely to occur.

Examples of the high-boiling point polar organic solvent include aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters, aromatic phosphoric acid esters, and the like. Of these high-boiling point polar organic solvents, the aromatic dicarboxylic acid diesters, the aromatic carboxylic acid esters, and the aliphatic dicarboxylic acid diesters, polyalkylene glycol diethers are preferable, and from the viewpoint that thermal degradation is less likely to occur, polyalkylene glycol diethers are more preferable. The high-boiling point polar organic solvents may be used alone or in combination of two or more.

Examples of the aromatic dicarboxylic acid diesters include phthalic acid esters such as dibutyl phthalate, dioctyl phthalate, dibenzyl phthalate, and benzyl butyl phthalate. Examples of the aromatic carboxylic acid esters include benzoic acid esters such as benzyl benzoate. Examples of the aliphatic dicarboxylic acid diesters include adipic acid esters such as dioctyl adipate and sebacic acid esters such as dibutyl sebacate.

Examples of the polyalkylene glycol diethers include compounds represented by the following formula (1):

$$X^1—O—(R^1—O)_p—Y^1 \qquad (1)$$

(in the formula (1), $R^1$ represents a methylene group or a linear or branched alkylene group having 2 to 8 carbon atoms, $X^1$ represents a hydrocarbon group, $Y^1$ represents an alkyl group having 2 to 20 carbon atoms or an aryl group having 6 to 20 carbon atoms, p is an integer of 1 or larger, and when p is 2 or larger, a plurality of $R^1$s may be the same or different from each other).

$R^1$ in the formula (1) is not particularly limited, as long as $R^1$ is a methylene group or a linear or branched alkylene group having 2 to 8 carbon atoms. $R^1$ in the formula (1) is preferably an ethylene group, from the viewpoint that the polyalkylene glycol diether represented by the formula (1) is readily available or is easily synthesized.

$X^1$ in the formula (1) is a hydrocarbon group such as an alkyl group or an aryl group. Of these hydrocarbon groups, $X^1$ in the formula (1) is preferably a hydrocarbon group having 1 to 20 carbon atoms. If the number of carbon atoms of the hydrocarbon group exceeds the upper limit, the polarity of the polyalkylene glycol diether represented by the formula (1) tends to be low. As a result, the solubility of the glycolic acid oligomer tends to be lowered, and the co-distilling off with the glycolide tends to be difficult. Examples of the alkyl group include a methyl group, an ethyl group, a propyl group, a butyl group, a pentyl group, a hexyl group, a heptyl group, an octyl group, a nonyl group, a decyl group, a lauryl group, and the like. These alkyl groups may be branched or linear. Examples of the aryl group include a phenyl group, a naphthyl group, substituted phenyl groups, substituted naphthyl groups, and the like. The substituents of the substituted phenyl groups and the substituted naphthyl groups are each preferably an alkyl group, an alkoxy group, or a halogen atom (Cl, Br, I or the like). The number of the substituents is, for example, 1 to 5, and preferably 1 to 3, when the aryl group is a substituted phenyl group. When multiple substituents are present, the substituents may be the same or different from each other. Note that the substituents play a role of adjusting the boiling point and the polarity of the polyalkylene glycol diether.

$Y^1$ in the formula (1) is an alkyl group having 2 to 20 carbon atoms or an aryl group having 6 to 20 carbon atoms. If the number of carbon atoms in $Y^1$ exceeds the upper limit, the polarity of the polyalkylene glycol diether represented by the formula (1) is low. As a result, the solubility of the glycolic acid oligomer is lowered, and the co-distilling off with the glycolide becomes difficult. Meanwhile, if $Y^1$ is a methyl group, the number of carbon atoms in $R^1$ needs to be large in order that the polyalkylene glycol diether represented by the formula (1) is a solvent having a high boiling point appropriate for the co-distilling off with the glycolide. However, if such a polyalkylene glycol diether is synthesized, a production process is complicated because the distribution of p is broad, necessitating purification by distillation and the like. Accordingly, polyalkylene glycol diethers whose $Y^1$ in the formula (1) is a methyl group are not preferable, from the viewpoint of carrying out the invention in an industrial scale. Examples of the alkyl group include those described as the examples of the alkyl group which can be $X^1$, and examples of the aryl group include those described as examples of the aryl group which can be $X^1$.

In the formula (1), p is an integer of 1 or larger, and is preferably an integer of 2 or larger. Meanwhile, an upper limit of p is not particularly limited, but is preferably an integer of 8 or smaller, and more preferably an integer of 5 or smaller. If p exceeds the upper limit, the distribution of the degrees of polymerization becomes broad when the polyalkylene glycol diether is synthesized. As a result, it tends to be difficult to isolate a polyalkylene glycol diether having the same p in the formula (1). In addition, when p is 2 or larger, a plurality of $R^1$s may be the same or different from each other.

Of these polyalkylene glycol diethers, polyalkylene glycol diethers are preferable in which $X^1$ and $Y^1$ in the formula (1) are both alkyl groups, and the total number of carbon atoms of $X^1$ and $Y^1$ is 3 to 21 (more preferably 6 to 20). In addition, in this case, $X^1$ and $Y^1$ may be the same alkyl groups, or different alkyl groups from each other.

Specific examples of the polyalkylene glycol diethers include
polyethylene glycol dialkyl ethers such as diethylene glycol dibutyl ether, diethylene glycol dihexyl ether, diethylene glycol dioctyl ether, diethylene glycol butyl-2-chlorophenyl ether, triethylene glycol diethyl ether, triethylene glycol dipropyl ether, triethylene glycol dibutyl ether, triethylene glycol dihexyl ether, triethylene glycol dioctyl ether, triethylene glycol butyl octyl ether, triethylene glycol butyl decyl ether, tetraethylene glycol diethyl ether, tetraethylene glycol dipropyl ether, tetraethylene glycol dibutyl ether, tetraethylene glycol dihexyl ether, tetraethylene glycol dioctyl ether, diethylene glycol butyl hexyl ether, diethylene glycol butyl octyl ether, diethylene glycol hexyl octyl ether, triethylene glycol butyl hexyl ether, triethylene glycol hexyl octyl ether, tetraethylene glycol butyl hexyl ether, tetraethylene glycol butyl octyl ether, and tetraethylene glycol hexyl octyl ether; polyalkylene glycol dialkyl ethers having propyleneoxy groups or butyleneoxy groups with which the ethyleneoxy groups in the above-described polyethylene glycol dialkyl ethers are replaced (for example, polypropylene glycol dialkyl ethers and polybutylene glycol dialkyl ethers); polyethylene glycol alkyl aryl ethers such as diethylene glycol butyl phenyl ether, diethylene glycol hexyl phenyl ether, diethylene glycol octyl phenyl ether, triethylene glycol butyl phenyl ether, triethylene glycol hexyl phenyl ether, triethylene glycol octyl phenyl ether, tetraethylene glycol butyl phenyl ether, tetraethylene glycol hexyl phenyl ether, tetraethylene glycol octyl phenyl ether, and compounds having an alkyl group, an alkoxy group, a halogen atom, or the like with which a hydrogen atom of the phenyl group in these polyethylene glycol alkyl phenyl ethers is substituted;
polyalkylene glycol alkyl aryl ethers having propyleneoxy groups or butyleneoxy groups with which the ethyleneoxy groups in the above-described polyethylene glycol alkyl aryl ethers are replaced (for example, polypropylene glycol alkyl aryl ethers and polybutylene glycol alkyl aryl ethers); polyethylene glycol diaryl ethers such as diethylene glycol diphenyl ether, triethylene glycol diphenyl ether, tetraethylene glycol diphenyl ether, and compounds having an alkyl group, an alkoxy group, a halogen atom, or the like with which a hydrogen atom of a phenyl group in these polyethylene glycol diphenyl ethers is substituted; polyalkylene glycol diaryl ethers having propyleneoxy groups or butyleneoxy groups with which the ethyleneoxy groups in the above-described polyethylene glycol diaryl ethers are replaced (for example, polypropylene glycol diaryl ethers and polybutylene glycol diaryl ethers); and the like. These polyalkylene glycol diethers can be synthesized by the method described in International Publication No. WO02/014303.

Of these polyalkylene glycol diethers, polyalkylene glycol dialkyl ethers are preferable, and diethylene glycol dialkyl ethers, triethylene glycol dialkyl ethers, and tetraethylene glycol dialkyl ethers are more preferable, from the viewpoints that synthesis is easy and thermal degradation is less likely to occur.

In addition, the polyalkylene glycol diether used in the present invention is preferably such that the solubility of glycolide in the polyalkylene glycol diether at 25° C. is 0.1 to 10%. Note that the solubility of glycolide is represented by a percentage of the mass (g) of glycolide to the volume (ml) of a polyalkylene glycol diether in a case where glycolide is dissolved in the polyalkylene glycol diether at 25° C. until a saturated state. If the solubility of glycolide is less than the lower limit, the glycolide co-distilled off with the polyalkylene glycol diether tends to deposit at an intermediate portion of a production line, causing blocking of the production line and the like. Meanwhile, if the solubility of glycolide exceeds the upper limit, it may be necessary, in some cases, to isolate the glycolide by, for example, cooling the co-distillate until 0° C. or below or adding a poor solvent to the co-distillate for the recovery of the co-distilled glycolide.

Examples of the polyalkylene glycol diether in which glycolide has such a predetermined solubility include tetraethylene glycol dibutyl ether (boiling point=340° C., molecular weight=306, solubility of glycolide=4.6%), triethylene glycol butyl octyl ether (boiling point=350° C., molecular weight=350, solubility of glycolide=2.0%), triethylene glycol butyl decyl ether (boiling point=400° C., molecular weight=400, solubility of glycolide=1.3%), diethylene glycol dibutyl ether (boiling point=256° C., molecular weight=218, solubility of glycolide=1.8%), and diethylene glycol butyl 2-chlorophenyl ether (boiling point=345° C., molecular weight=273, solubility of glycolide=1.8%). Of these polyalkylene glycol diethers, tetraethylene glycol dibutyl ether and triethylene glycol butyl octyl ether are more preferable, from the viewpoints of easiness of synthesis, thermal degradation resistance, depolymerization reactivity, recoverability of glycolide, and the like.

In the present invention, a content of the high-boiling point polar organic solvent in the mixture containing the glycolic acid oligomer, the high-boiling point polar organic solvent, the tin compound, and, when necessary, the solubilizing agent is preferably 30 to 5000 parts by mass, more preferably 50 to 2000 parts by mass, and particularly preferably 60 to 200 parts by mass, relative to 100 parts by mass of the glycolic acid oligomer. If the content of the high-boiling point polar organic solvent is less than the lower limit, the ratio of a solution phase of the glycolic acid oligomer in the mixture according to the present invention under the depolymerization temperature condition tends to be lowered (the ratio of a melt phase of the glycolic acid oligomer is increased), and thereby the depolymerization reactivity of the glycolic acid oligomer tends to be lowered. Meanwhile, if the content of the high-boiling point polar organic solvent exceeds the upper limit, the thermal efficiency during the depolymerization reaction tends to be lowered, and the productivity of the glycolide by the depolymerization reaction tends to be lowered.

(3) Tin Compound

Examples of the tin compound used in the present invention include tin dichloride, tin tetrachloride, tin alkylcarboxylates, and the like. The use of the tin compound suppresses the production of glycolic acid, an open-chain dimer thereof, and the like during the depolymerization reaction, making it possible to obtain glycolide having a higher purity than the purity achieved in a case where no tin compound is used, and to greatly increase the yield of glycolide.

These tin compounds may be used alone or in combination of two or more. Of the above-described tin compounds, tin dichloride or tin octanoate is preferable, and tin octanoate is more preferable, from the viewpoint of the purity and productivity of the obtained glycolide.

In the present invention, a content of the tin compound in the mixture containing the glycolic acid oligomer, the high-boiling point polar organic solvent, the tin compound, and, when necessary, the solubilizing agent is preferably 0.01 to 10 parts by mass, more preferably 0.05 to 2 parts by mass, and particularly preferably 0.1 to 0.5 parts by mass, relative to 100 parts by mass of the glycolic acid oligomer. If the content of the tin compound is less than the lower limit, the production of glycolic acid, an open-chain dimer thereof, and the like during the depolymerization reaction tends to be insufficiently suppressed, resulting in a tendency that the purity of glycolide is not improved, and the yield of glycolide tends to be insufficiently increased. Meanwhile, if the content of the tin compound exceeds the upper limit, the decomposition reaction of the high-boiling point polar solvent or the solubilizing agent tends to be accelerated, and decomposed products tend to be co-distilled off with glycolide, resulting in a tendency that the purity of glycolide is lowered.

(4) Solubilizing Agent

In the present invention, the solubilizing agent is preferably added to the mixture containing the glycolic acid oligomer, the high-boiling point polar organic solvent, and the tin compound, in order to improve the dissolution characteristics (solubility and/or dissolution rate) of the glycolic acid oligomer in the high-boiling point polar organic solvent. In addition, the addition of the solubilizing agent can also enhance the depolymerization reactivity of the glycolic acid oligomer. The solubilizing agent is preferably a compound satisfying any one or more of the following requirements (1) to (5).

(1) being a non-basic compound. Note that basic compounds such as amines, pyridine, and quinoline are not preferable, because these basic compounds may react with the glycolic acid oligomer or the formed glycolide.

(2) being a compound miscible with or soluble in the high-boiling point polar organic solvent. The compound may be liquid or solid at normal temperature, as long as the compound is miscible or soluble in the high-boiling point polar organic solvent.

(3) being a compound having a boiling point of 180° C. or higher, preferably 200° C. or higher, more preferably 230° C. or higher, and particularly preferably 250° C. or higher. In particular, it is preferable to use, as the solubilizing agent, a compound having a boiling point higher than the boiling point of the high-boiling point polar organic solvent used for the depolymerization reaction, because the compound is not distilled off at all or the amount of the compound distilled off is extremely small during the co-distilling off of glycolide and the high-boiling point polar organic solvent. In many cases, favorable results can be obtained by using a compound having a boiling point of 450° C. or higher as the solubilizing agent. However, alcohols and the like can be preferably used as the solubilizing agent, even when the alcohols and the like are compounds having a boiling point lower than the boiling point of the high-boiling point polar organic solvent used for the depolymerization reaction.

(4) being a compound having a functional group, such as an OH group, a COOH group, or a CONH group, for example.

(5) having a higher affinity for the glycolic acid oligomer than the affinity of the high-boiling point polar organic solvent for the glycolic acid oligomer. Note that the affinity of the solubilizing agent for the glycolic acid oligomer can be checked as follows. Specifically, a mixture of the glycolic acid oligomer and the high-boiling point polar organic solvent is heated until a temperature of 230° C. or higher to form a homogeneous solution phase. Then, the concentration of the glycolic acid oligomer is increased by further adding the glycolic acid oligomer to the solution phase, until the mixture does not form a homogeneous solution phase any more. Then, the solubilizing agent is added thereto, and whether or not a homogeneous solution phase is formed again is visually observed.

In the present invention, a compound satisfying any one or more of these requirements is used as the solubilizing agent. Specifically, at least one non-basic organic compound which is selected from the group consisting of alcohols, phenols, aliphatic carboxylic acids, aliphatic amides, aliphatic imides, polyalkylene glycol diethers having a molecular weight exceeding 450, and sulfonic acids, and which has a boiling point of 180° C. or higher (preferably 200° C. or higher, more preferably 230° C. or higher, and particularly preferably 250° C. or higher) is used as the solubilizing agent.

Of these solubilizing agents, alcohols are particularly effective. Examples of the alcohols include aliphatic alcohols such as decanol, tridecanol, decanediol, ethylene glycol, propylene glycol, and glycerin; aromatic alcohols such as cresol, chlorophenol, and naphthyl alcohol; polyalkylene glycols; polyalkylene glycol monoethers; and the like. These alcohols may be used alone or in combination of two or more.

Moreover, of these alcohols, a polyalkylene glycol monoether represented by the following formula (2) is preferable:

$$HO-(R^2-O)_q-X^2 \quad (2)$$

(in the formula (2), $R^2$ represents a methylene group or a linear or branched alkylene group having 2 to 8 carbon atoms, $X^2$ represents a hydrocarbon group, q is an integer of 1 or larger, and when q is 2 or larger, a plurality of $R^2$s may be the same or different from each other). This is because the polyalkylene glycol monoether is hardly distilled off due to the high boiling point. This is also because of the high solubility of the glycolic acid oligomer in the polyalkylene glycol monoether, acceleration of the depolymerization reaction, and a particularly excellent effect of cleaning an inner wall of a reaction vessel.

$R^2$ in the formula (2) is not particularly limited, as long as $R^2$ is a methylene group or a linear or branched alkylene group having 2 to 8 carbon atoms. $R^2$ is preferably an ethylene group from the viewpoint that the polyalkylene glycol diether represented by the formula (2) is readily available or is easily synthesized.

$X^2$ in the formula (2) is a hydrocarbon group such as an alkyl group or an aryl group. Of these, $X^2$ is preferably a hydrocarbon group having 1 to 18 carbon atoms, and more preferably a hydrocarbon group having 6 to 18 carbon atoms.

Of these polyalkylene glycol monoethers, preferred are polyethylene glycol monoalkyl ethers such as polyethylene glycol monomethyl ether, polyethylene glycol monoethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; and polyalkylene glycol monoalkyl ethers having propyleneoxy groups or butyleneoxy groups with which the ethyleneoxy groups in the above-described polyethylene glycol monoalkyl ethers are replaced (for example, polypropylene glycol monoalkyl ethers and polybutylene glycol monoalkyl ethers), and more preferred are polyethylene glycol monohexyl ether, polyethylene glycol monooctyl ether, polyethylene glycol monodecyl ether, and polyethylene glycol monolauryl ether; and polyalkylene glycol monoethers having propyleneoxy groups or butyleneoxy groups with which the ethyleneoxy groups in the above-described polyethylene glycol monoalkyl ethers are replaced. These polyalkylene glycol monoethers may be used alone, or in combination of two or more.

Moreover, examples of other preferred alcohols include polyalkylene glycols represented by the following formula (3):

$$HO-(R^3-O)_r-H \quad (3)$$

(in the formula (3), $R^3$ represents a methylene group or a linear or branched alkylene group having 2 to 8 carbon atoms, r is an integer of 1 or larger, and when r is 2 or larger, a plurality of $R^2$s may be the same or different from each other).

$R^3$ in the formula (3) is not particularly limited, as long as $R^3$ is a methylene group or a linear or branched alkylene group having 2 to 8 carbon atoms. $R^3$ is preferably an ethylene group from the viewpoint that the polyalkylene glycol represented by the formula (3) is readily available or is easily synthesized.

Examples of the polyalkylene glycols include polyethylene glycol, polypropylene glycol, polybutylene glycol, and the like. These polyalkylene glycols may be used alone or in combination of two or more.

Examples of the polyalkylene glycol diethers having a molecular weight exceeding 450 used as the solubilizing agent include polyethylene glycol dimethyl ether #500 (average molecular weight: 500), polyethylene glycol dimethyl ether #2000 (average molecular weight: 2000), and the like. If the molecular weight is less than the lower limit, the solubilizing agent is also distilled off together with the distilling-off of glycolide during the depolymerization reaction, resulting in a tendency that the solubility of the glycolic acid oligomer in the mixture according to the present invention is lowered.

Note that the action of the solubilizing agent in the depolymerization reaction of the glycolic acid oligomer is not sufficiently clarified as of now; however, the present inventors presume as follows. Specifically, the solubilizing agent presumably exerts 1) an action of reacting with terminals of the glycolic acid oligomer, to thereby convert the glycolic acid oligomer to a more soluble material (state), 2) an action of adjusting the molecular weight of the glycolic acid oligomer by acting on internal portions of molecule chains of the glycolic acid oligomer and cleaving the molecular chains, to thereby convert the glycolic acid oligomer to a more soluble material, 3) an action of increasing the hydrophilicity of the entire solvent system by changing the polarity of the solvent system, to thereby increase the solubility of the glycolic acid oligomer, 4) an action of emulsifying and dispersing the glycolic acid oligomer, 5) an action of binding to one of the terminals of the glycolic acid oligomer, to thereby increase the number of depolymerization reaction points, 6) an action of cleaving the glycolic acid oligomer by acting on internal portions thereof, and binding to terminals of the cleaved molecular chains, to thereby increase the number of depolymerization reaction points, and 7) a combined action of these actions.

In the present invention, a content of the solubilizing agent in the mixture containing the glycolic acid oligomer, the high-boiling point polar organic solvent, the tin compound, and the solubilizing agent is preferably 0.1 to 500 parts by mass and more preferably 1 to 300 parts by mass relative to 100 parts by mass of the glycolic acid oligomer. If the content of the solubilizing agent is less than the lower limit, the dissolution characteristics of the glycolic acid oligomer in the high-boiling point polar organic solvent may be lowered. Meanwhile, a content of the solubilizing agent exceeding the upper limit tends to be not preferable in terms of economy, because the recovery of the solubilizing agent requires a lot of costs.

<Method for Producing Glycolide>

A method for producing glycolide of the present invention comprises the steps of:

heating a mixture containing the glycolic acid oligomer, the high-boiling point polar organic solvent, and the tin compound under predetermined conditions, to thereby form glycolide by depolymerization of the glycolic acid oligomer in a solution; and co-distilling off the formed glycolide and the high-boiling point polar organic solvent from a depolymerization reaction system.

Hereinafter, the method for producing glycolide of the present invention is described specifically.

(Dissolving Step)

First, the glycolic acid oligomer, the high-boiling point polar organic solvent, and the tin compound are mixed with each other, and the obtained mixture is heated to dissolve the glycolic acid oligomer in the high-boiling point polar organic solvent. The formation of a solution phase by dissolving the glycolic acid oligomer in the high-boiling point polar organic solvent as described above dramatically increases the formation rate and the volatilization rate of glycolide in the depolymerization reaction of the glycolic acid oligomer, which will be described later. On the other hand, if the glycolic acid oligomer is insufficiently dissolved, the glycolic acid oligomer forms a melt phase, and the glycolide is difficult to distill off. In such a case, it is preferable to increase the solubility of the glycolic acid oligomer by adding the solubilizing agent.

A temperature during the heating is not particularly limited, as long as the glycolic acid oligomer is depolymerized at the temperature. The temperature is preferably 200 to 350° C., more preferably 210 to 310° C., particularly preferably 220 to 300° C., and most preferably 230 to 290° C. If the heating temperature is lower than the lower limit, the glycolic acid oligomer is not easily dissolved in the high-boiling point polar organic solvent, resulting in a tendency that a homogeneous solution cannot be obtained, or that the formed glycolide cannot be distilled off. Meanwhile, if the heating temperature exceeds the upper limit, the glycolic acid oligomer tends to be heavy components.

The heating of the mixture as described above may be conducted under normal pressure or reduced pressure, and is preferably conducted under a reduced pressure of 0.1 to 90 kPa (more preferably 1 to 30 kPa, particularly preferably 1.5 to 20 kPa, and most preferably 2 to 10 kPa). In addition, it is also preferable to conduct the heating under an inert gas atmosphere.

When the glycolic acid oligomer is dissolved in the high-boiling point polar organic solvent as described above, it is preferable to form a homogeneous solution phase. However, the melt phase of the glycolic acid oligomer may be remained, as long as the ratio of the remaining melt phase of the glycolic acid oligomer is 0.5 or less. Note that the term "the ratio of the remaining melt phase" means a ratio represented by b/a, where a (ml) is the volume of the melt phase of a glycolic acid oligomer formed when F (g) of the glycolic acid oligomer is added to a solvent, such as liquid paraffin, which is substantially incapable of dissolving the glycolic acid oligomer, and then the materials are heated until a temperature at which the glycolic acid oligomer is depolymerized; and b (ml) is the volume of the melt phase of the glycolic acid oligomer formed when F (g) of the glycolic acid oligomer is added to a high-boiling point polar organic solvent to be actually used, and then the materials are heated until the temperature at which the glycolic acid oligomer is depolymerized. The ratio of the remaining melt phase is more preferably 0.3 or less, particularly preferably 0.1 or less, and most preferably substantially zero. If the ratio of the remaining melt phase exceeds the upper limit, the purity of glycolide tends to be lowered.

(Depolymerization Step)

Next, the solution phase in which the glycolic acid oligomer is substantially homogeneously dissolved in the high-boiling point polar organic solvent as described above continues to be heated. Thus, the glycolic acid oligomer is depolymerized in the solution phase, and glycolide is formed. Preferred conditions of the temperature, the pressure, and the like for the depolymerization reaction are the same as the preferred conditions for the dissolving step. In addition, the heating conditions in the dissolving step may be the same as or different from the heating conditions in the depolymerization step. In particular, the pressure is preferably set as low as possible, from the viewpoint that the depolymerization reaction temperature is lowered, and the recovery ratio of the solvent is improved. In general, the heating is conducted at a pressure lower than the pressure in the dissolving step.

(Distilling-Off Step)

The thus formed glycolide is distilled off together with the high-boiling point polar organic solvent. This makes it possible to suppress the adherence of glycolide to an inner wall of a production line, and to prevent of the blocking or the like. In addition, the depolymerization reaction is a reversible reaction. Hence, the depolymerization reaction of the glycolic acid oligomer proceeds efficiently by the distilling-off of the glycolide from the reaction system. Particularly when the depolymerization reaction is conducted under a reduced pressure, the glycolide is easily distilled off, and the depolymerization reaction proceeds more efficiently. Moreover, the tin compound is present in the reaction system in the present invention. Hence, the equilibrium of the depolymerization reaction is shifted to the formation of the glycolide, and the depolymerization reaction proceeds more efficiently. Presumably because of these factors, the yield of glycolide is greatly increased.

When glycolide is continuously produced by the production method of the present invention, the glycolic acid oligomer in an amount corresponding to the amount of the glycolide distilled off is preferably supplied continuously or intermittently to depolymerization reaction system. In this case, it is necessary to supply the glycolic acid oligomer such that the state where the glycolic acid oligomer is homogeneously dissolved in the high-boiling point polar organic solvent can be kept. In addition, when the high-boiling point polar organic solvent or the solubilizing agent is distilled off, the high-boiling point polar organic solvent or the solubilizing agent in an amount corresponding to the amount of the high-boiling point polar organic solvent or the solubilizing agent distilled off is preferably supplied continuously or intermittently to the depolymerization reaction system. Note that a fresh high-boiling point polar organic solvent and a fresh solubilizing agent may be supplied as the high-boiling point polar organic solvent and the solubilizing agent. Alternatively, those recovered in the following recovery step may be reused as the high-boiling point polar organic solvent and the solubilizing agent.

(Recovery Step)

The glycolide distilled off together with the high-boiling point polar organic solvent as described above can be recovered by a method described in Japanese Unexamined Patent Application Publication No. 2004-523596 or International Publication No. WO02/014303. For example, the glycolide can be recovered by cooling a co-distillate of the glycolide and the high-boiling point polar organic solvent, and, when necessary, adding a poor solvent, for solidification and deposition. Alternatively, as described in International Publication No. WO02/014303, the glycolide can also be recovered by phase separation, when a high-boiling point polar organic solvent having an excellent heat stability is used.

The thus recovered glycolide may be further purified to increase the purity. The glycolide obtained by the production method of the present invention has already had a high purity at the time of the distilling-off. Hence, when conducted, a purification treatment can be conducted with a reduced load.

EXAMPLES

Hereinafter, the present invention will be described more specifically on the basis of Examples and Comparative Examples. However, the present invention is not limited to Examples below. Note that the melting point of a glycolic acid oligomer and the purity of a glycolide were measured by the following methods.

<Melting Points of Glycolic Acid Oligomers>

The melting point was measured by using a differential scanning calorimeter (DSC) under an inert gas atmosphere and under a condition of a rate of temperature rise of 10° C./minute.

<Purities of Glycolides>

The purity was measured by gas chromatography (GC) by using 4-chlorobenzophenone as an internal standard solution.

Preparation Example 1

To a 1-liter separable flask, 1 kg of a 70% aqueous solution of glycolic acid (manufactured by Du Pont, industrial grade) was supplied, and heated at normal pressure with stirring to raise the temperature from room temperature to 220° C. over 4 hours. During this period, a condensation reaction was conducted, while water produced was removed by distillation. Next, the pressure inside the flask was gradually reduced from normal pressure to 2 kPa over 1 hour, and then the condensation reaction was continued by heating at 220° C. for 3 hours. After that, low boiling components such as unreacted raw materials were removed by distillation. Thus, 480 g of a glycolic acid oligomer (GAO) was obtained. The glycolic acid oligomer had a melting point of 211° C.

Example 1

To a 500-ml flask, 160 g of the glycolic acid oligomer (GAO) obtained in Preparation Example 1, 100 g of tetraethylene glycol dibutyl ether (TEG-DB, boiling point: 340° C., molecular weight: 306, solubility of glycolide: 4.6%) as a solvent, 89 g of octyl triethylene glycol (OTEG) as a solubilizing agent, and 0.25 g of tin dichloride ($SnCl_2$) as a catalyst were supplied, and heated until 230° C. Thus, a homogeneous solution was prepared.

A depolymerization reaction was conducted by reducing the pressure until 3.0 kPa, with the solution kept at 230° C., and the formed glycolide was co-distilled off with tetraethylene glycol dibutyl ether. Here, the depolymerization reaction was continued for 10 hours, while the amount of glycolide distilled off was measured every one hour, and the glycolic acid oligomer in an amount corresponding to the distilled-off amount was added to the flask.

The purity of the obtained glycolide was measured, and an average purity (unit: % by mass) over the entire reaction time (between the 0th hour and the 10th hour) was calculated. Table 1 shows the results. Table 1 also shows the amount of glycolide distilled off between the 9th hour and the 10th hour.

Comparative Example 1

A depolymerization reaction was conducted for 10 hours in the same manner as in Example 1, except that no catalyst was used. Table 1 shows the average purity of the obtained glycolide (between the 0th hour and the 10th hour) and the amount of glycolide distilled off (between the 9th hour and the 10th hour).

Example 2

A depolymerization reaction was conducted for 10 hours in the same manner as in Example 1, except that the amount of the glycolic acid oligomer (GAO) initially supplied was changed from 160 g to 87 g. Table 1 shows the average purity of the obtained glycolide (between the 0th hour and the 10th hour) and the amount of glycolide distilled off (between the 9th hour and the 10th hour).

Comparative Example 2

A depolymerization reaction was conducted for 10 hours in the same manner as in Example 2, except that no catalyst was used. Table 1 shows the average purity of the obtained glycolide (between the 0th hour and the 10th hour) and the amount of glycolide distilled off (between the 9th hour and the 10th hour).

Example 3

A depolymerization reaction was conducted for 10 hours in the same manner as in Example 1, except that the amount of tetraethylene glycol dibutyl ether (TEG-DB) initially supplied was changed from 100 g to 50 g. Table 1 shows the average purity of the obtained glycolide (between the 0th hour and the 10th hour) and the amount of glycolide distilled off (between the 9th hour and the 10th hour).

Comparative Example 3

A depolymerization reaction was conducted for 10 hours in the same manner as in Example 3, except that no catalyst was used. Table 1 shows the average purity of the obtained glycolide (between the 0th hour and the 10th hour) and the amount of glycolide distilled off (between the 9th hour and the 10th hour).

Example 4

A depolymerization reaction was conducted for 10 hours in the same manner as in Example 1, except that the amount of tin dichloride ($SnCl_2$) initially supplied was changed from 0.25 g to 0.06 g. Table 1 shows the average purity of the obtained glycolide (between the 0th hour and the 10th hour) and the amount of glycolide distilled off (between the 9th hour and the 10th hour).

Example 5

A depolymerization reaction was conducted for 10 hours in the same manner as in Example 1, except that the amount of tin dichloride ($SnCl_2$) initially supplied was changed from 0.25 g to 0.02 g. Table 1 shows the average purity of the obtained glycolide (between the 0th hour and the 10th hour) and the amount of glycolide distilled off (between the 9th hour and the 10th hour).

Example 6

A depolymerization reaction was conducted for 10 hours in the same manner as in Example 1, except that 0.45 g of tin octanoate ($Sn(Oct)_2$) was used instead of tin dichloride ($SnCl_2$). Table 1 shows the average purity of the obtained glycolide (between the 0th hour and the 10th hour) and the amount of glycolide distilled off (between the 9th hour and the 10th hour).

Example 7

A depolymerization reaction was conducted for 10 hours in the same manner as in Example 1, except that 0.17 g of tin oxide ($SnO_2$) was used instead of tin dichloride ($SnCl_2$). Table 1 shows the average purity of the obtained glycolide (between the 0th hour and the 10th hour) and the amount of glycolide distilled off (between the 9th hour and the 10th hour).

Comparative Example 4

A depolymerization reaction was conducted for 10 hours in the same manner as in Example 1, except that no solvent was used. Table 1 shows the average purity of the obtained glycolide (between the 0th hour and the 10th hour) and the amount of glycolide distilled off (between the 9th hour and the 10th hour).

Comparative Example 5

A homogeneous solution was prepared in the same manner as in Example 1, except that 300 g of acetone was used instead of tetraethylene glycol dibutyl ether (TEG-DB). A depolymerization reaction was conducted at normal pressure under a nitrogen stream, with this solution being kept at 210° C., and the formed glycolide was co-distilled off with acetone. Here, the depolymerization reaction was continued for 10 hours, while the glycolic acid oligomer was added to the flask in the same manner as in Example 1. Table 1 shows the average purity of the obtained glycolide (between the 0th hour and the 10th hour) and the amount of glycolide distilled off (between the 9th hour and the 10th hour).

TABLE 1

|  | Initial feed amount (g) | | | Average purity (% by mass) | Amount distilled-off (g/hour) |
| --- | --- | --- | --- | --- | --- |
|  | GAO | Solvent | Sn compound | [between 0th hour and 10th hour] | [between 9th hour and 10th hour] |
| Ex. 1 | 160 | TEG-DB 100 | $SnCl_2$ 0.25 | 93.4 | 27.8 |
| Comp. Ex. 1 | 160 | TEG-DB 100 | Not added | 88.4 | 19.2 |
| Ex. 2 | 87 | TEG-DB 100 | $SnCl_2$ 0.25 | 92.0 | 21.7 |
| Comp. Ex. 2 | 87 | TEG-DB 100 | Not added | 88.7 | 17.1 |
| Ex. 3 | 160 | TEG-DB 50 | $SnCl_2$ 0.25 | 96.1 | 32.0 |
| Comp. Ex. 3 | 160 | TEG-DB 50 | Not added | 86.6 | 24.1 |
| Ex. 4 | 160 | TEG-DB 100 | $SnCl_2$ 0.06 | 94.4 | 23.9 |
| Ex. 5 | 160 | TEG-DB 100 | $SnCl_2$ 0.02 | 92.0 | 21.7 |
| Ex. 6 | 160 | TEG-DB 100 | $Sn(Oct)_2$ 0.45 | 96.3 | 29.2 |
| Ex. 7 | 160 | TEG-DB 100 | $SnO_2$ 0.17 | 90.5 | 21.7 |
| Comp. Ex. 4 | 160 | — 0 | $SnCl_2$ 0.25 | 81.0 | 13.0 |
| Comp. Ex. 5 | 160 | Acetone 300 | $SnCl_2$ 0.25 | 83.5 | 16.5 |

As is apparent from the results shown in Table 1, the average purity of glycolide was higher, and the amount of glycolide distilled off was larger in the cases where tin dichloride, which is the tin compound according to the present invention, was added (Examples 1 to 7) than in the cases where no tin compound was added (Comparative Example 1 to 3), than in the case where no solvent was used (Comparative Example 4), and than in the case where acetone was used as the solvent (Comparative Example 5).

INDUSTRIAL APPLICABILITY

As described above, according to the present invention, it is possible to improve the purity of glycolide, and greatly increase the yield of glycolide in a case where glycolide is produced by depolymerization of a glycolic acid oligomer in a solution phase.

Accordingly, the purity of the glycolide obtained by the method for producing glycolide of the present invention is high. Hence, problems such as the blocking of a production line are less likely to occur, and a large amount of glycolide can be produced stably for a long period. Consequently, the method for producing glycolide of the present invention is useful as an industrially advantageous method for producing glycolide.

The invention claimed is:

1. A method for producing glycolide, comprising the steps of:
heating a mixture containing a glycolic acid oligomer, a high-boiling point polar organic solvent having a boiling point of 230 to 450° C., and a tin compound under normal pressure or reduced pressure until a temperature at which the glycolic acid oligomer is depolymerized, to thereby dissolve the glycolic acid oligomer in the high-boiling point polar organic solvent;
heating a solution, in which the glycolic acid oligomer is dissolved, under normal pressure or reduced pressure until a temperature at which the glycolic acid oligomer is depolymerized, to thereby form glycolide by depolymerization of the glycolic acid oligomer in the solution; and
co-distilling off the high-boiling point polar organic solvent and the formed glycolide from a depolymerization reaction system.

2. The method for producing glycolide according to claim 1, wherein the tin compound is tin dichloride or tin octanoate.

3. The method for producing glycolide according to claim 1, wherein the high-boiling point polar organic solvent is a polyalkylene glycol diether which is represented by the following formula (1) and which has a molecular weight of 150 to 450:

$$X^1\text{—}O\text{—}(R^1\text{—}O)_p\text{—}Y^1 \qquad (1)$$

(in the formula (1), $R^1$ represents a methylene group or a linear or branched alkylene group having 2 to 8 carbon atoms, $X^1$ represents a hydrocarbon group having 1 to 20 carbon atoms, $Y^1$ represents an alkyl group having 2 to 20 carbon atoms or an aryl group having 6 to 20 carbon atoms, p is an integer of 1 or larger, and when p is 2 or larger, a plurality of $R^1$s may be the same or different from each other).

4. The method for producing glycolide according to claim 1, wherein the mixture further contains at least one solubilizing agent having a boiling point of 180° C. or higher which is selected from the group consisting of alcohols, phenols, aliphatic carboxylic acids, aliphatic amides, aliphatic imides, polyalkylene glycol diethers having a molecular weight exceeding 450, and sulfonic acids.

5. The method for producing glycolide according to claim 4, wherein the solubilizing agent is a polyalkylene glycol monoether represented by the following formula (2):

$$HO\text{—}(R^2\text{—}O)_q\text{—}X^2 \qquad (2)$$

(in the formula (2), $R^2$ represents a methylene group or a linear or branched alkylene group having 2 to 8 carbon atoms, $X^2$ represents a hydrocarbon group having 1 to 18 carbon atoms, q is an integer of 1 or larger, and when q is 2 or larger, a plurality of $R^2$s may be the same or different from each other).

6. The method for producing glycolide according to claim 2, wherein the high-boiling point polar organic solvent is a polyalkylene glycol diether which is represented by the following formula (1) and which has a molecular weight of 150 to 450:

$$X^1\text{—}O\text{—}(R^1\text{—}O)_p\text{—}Y^1 \qquad (1)$$

(in the formula (1), $R^1$ represents a methylene group or a linear or branched alkylene group having 2 to 8 carbon atoms, $X^1$ represents a hydrocarbon group having 1 to 20 carbon atoms, $Y^1$ represents an alkyl group having 2 to 20 carbon atoms or an aryl group having 6 to 20 carbon atoms, p is an integer of 1 or larger, and when p is 2 or larger, a plurality of $R^1$s may be the same or different from each other).

7. The method for producing glycolide according to claim 2, wherein the mixture further contains at least one solubilizing agent having a boiling point of 180° C. or higher which is selected from the group consisting of alcohols, phenols, aliphatic carboxylic acids, aliphatic amides, aliphatic imides, polyalkylene glycol diethers having a molecular weight exceeding 450, and sulfonic acids.

8. The method for producing glycolide according to claim 7, wherein the solubilizing agent is a polyalkylene glycol monoether represented by the following formula (2):

$$HO\text{—}(R^2\text{—}O)_q\text{—}X^2 \qquad (2)$$

(in the formula (2), $R^2$ represents a methylene group or a linear or branched alkylene group having 2 to 8 carbon atoms, $X^2$ represents a hydrocarbon group having 1 to 18 carbon atoms, q is an integer of 1 or larger, and when q is 2 or larger, a plurality of $R^2$s may be the same or different from each other).

9. The method for producing glycolide according to claim 3, wherein the mixture further contains at least one solubilizing agent having a boiling point of 180° C. or higher which is selected from the group consisting of alcohols, phenols, aliphatic carboxylic acids, aliphatic amides, aliphatic imides, polyalkylene glycol diethers having a molecular weight exceeding 450, and sulfonic acids.

10. The method for producing glycolide according to claim 9, wherein the solubilizing agent is a polyalkylene glycol monoether represented by the following formula (2):

$$HO\text{—}(R^2\text{—}O)_q\text{—}X^2 \qquad (2)$$

(in the formula (2), $R^2$ represents a methylene group or a linear or branched alkylene group having 2 to 8 carbon atoms, $X^2$ represents a hydrocarbon group having 1 to 18 carbon atoms, q is an integer of 1 or larger, and when q is 2 or larger, a plurality of $R^2$s may be the same or different from each other).

* * * * *